(12) United States Patent
Heisler et al.

(10) Patent No.: US 6,419,684 B1
(45) Date of Patent: Jul. 16, 2002

(54) END-CUTTING SHAVER BLADE FOR AXIAL RESECTION

(75) Inventors: Gary R. Heisler, Palm Harbor; Phillip J. Berman, Clearwater; Robert A. Van Wyk, Largo, all of FL (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 09/572,035

(22) Filed: May 16, 2000

(51) Int. Cl.$^7$ .............................................. A61B 17/32
(52) U.S. Cl. ...................... 606/170; 606/180; 604/22; 600/567
(58) Field of Search ............................ 606/1, 159, 170, 606/171, 180; 604/22; 600/564, 566, 567

(56) References Cited

U.S. PATENT DOCUMENTS

| 1,493,240 A | 5/1924 | Bohn |
|---|---|---|
| 2,369,925 A | 2/1945 | Smith |
| 3,614,953 A | 10/1971 | Moss |
| 3,618,611 A | 11/1971 | Urban |
| 3,815,604 A | 6/1974 | O'Malley et al. |
| 3,844,272 A | 10/1974 | Banko |
| 3,882,872 A | 5/1975 | Douvas et al. |
| 3,976,077 A | 8/1976 | Kerfoot, Jr. |
| 4,204,444 A | 5/1980 | Bonnell et al. |
| 4,274,414 A | 6/1981 | Johnson et al. |
| 4,512,344 A | 4/1985 | Barber |
| 4,517,977 A | 5/1985 | Frost |
| 4,600,006 A | 7/1986 | Baker |
| 4,649,919 A | 3/1987 | Thimsen et al. |
| 4,834,729 A | 5/1989 | Sjostrom |
| 4,838,853 A | 6/1989 | Parisi |
| 4,844,064 A | 7/1989 | Thimsen et al. |
| 5,007,917 A | 4/1991 | Evans |
| 5,112,299 A | 5/1992 | Pascaloff |
| 5,123,904 A | 6/1992 | Shimomura et al. |
| 5,456,689 A | 10/1995 | Kresch et al. |
| 5,474,532 A | 12/1995 | Steppe |
| 5,792,166 A | 8/1998 | Gordon et al. |
| 6,001,116 A * | 12/1999 | Heisler et al. .............. 606/170 |

OTHER PUBLICATIONS

Product Catalog, Linvatec Corporation, 1998, pp. A–3 Through A–9.

* cited by examiner

Primary Examiner—Michael H. Thaler
(74) Attorney, Agent, or Firm—Gene Warzecha

(57) ABSTRACT

An end-cutting arthroscopic shaver blade having a tubular inner member rotatable within a tubular outer member. The distal ends of each of the tubular members are provided with at least two notches each of which has longitudinally extending sides provided with cutting edges. In one of the embodiments the outer tubular member is provided with an arcuate extension in order to guide tissue toward the notches.

4 Claims, 5 Drawing Sheets

END-CUTTING SHAVER BLADE FOR AXIAL RESECTION

BACKGROUND OF THE INVENTION

1. Field of the Invention

The invention relates to a shaver blade for arthroscopic and endoscopic use comprising an elongated inner tubular member rotatable within an elongated outer tubular member. In particular, the invention relates an elongated end-cutting shaver blade for resecting tissue presented perpendicular to the axis of the device.

2. Description of the Prior Art

The use of elongated surgical cutting or resection instruments has become well accepted in performing closed surgery such as arthroscopic or, more generally, endoscopic surgery. In closed surgery, access to the surgical site is gained via one or more portals, and instruments used in the surgical procedure must be elongated to permit the distal ends of the instruments to reach the surgical site. Surgical cutting instruments for use in closed surgery—also known as "shavers"—conventionally have a straight, elongated outer tubular member terminating at a distal end having an opening in the end or side wall (or both) to form a cutting port or window and a straight, elongated inner tubular member concentrically disposed in the outer tubular member and having a distal end disposed adjacent the opening in the distal end of the outer tubular member. The distal end of the inner tubular member also has a window opening having a surface or edge for engaging tissue via the opening in the outer tubular member and in many cases (but not all) cooperates with the outer opening to shear, cut or trim tissue. In some cases, such as burrs, the opening in the outer tube merely allows access to the tissue and does not otherwise cooperate with the inner window. The inner tubular member is rotatably driven about its axis from its proximal end, normally via a handpiece having a small electric motor which is controlled by finger actuated switches on the handpiece, a foot switch or switches on a console supplying power to the handpiece. The distal end of the inner tubular member can have various configurations depending upon the surgical procedure to be performed, and the opening in the distal end of the outer tubular member has a configuration to cooperate with the particular configuration of the distal end of the inner tubular member. The various configurations and combinations of inner and outer members produce assemblies, the individual and combined components of which are referred to generically as shaver blades or cutting blades. Resected tissue is aspirated through the hollow lumen of the inner tubular member to be collected via a vacuum tube communicating with the handpiece.

The aforementioned elongated surgical cutting instruments have also been produced in angled configurations in which the distal tips of the inner and outer members are aligned and offset or bent at either a fixed or variable angle from the proximal ends of the aligned inner and outer members. Examples of fixed and variable angle rotary surgical instruments are shown in U.S. Pat. No. 4,646,738 (Trott) and U.S. Pat. No. 5,411,514 (Fucci et al.), both assigned to the assignee hereof, and incorporated by reference herein. In other respects the operation of fixed and variable angle shavers is largely the same as that of the straight shavers described above.

Shaver blades are usually optimized for a particular surgical procedure or part thereof. Thus, during a procedure a surgeon may use shaver blades optimized for cutting various types of tissue. Certain tissue, because of its particular anatomical position is best resected by a shaver blade designed for such tissue. Thus, end-cutting shaver blades are used for certain applications where the tissue to be resected is in line with the axis of the blade, or nearly in line. That is, the inner and outer windows are so aligned that tissue situated in a plane perpendicular to the blade axis may be introduced to the windows and resected. The invention relates to improvements in end-cutting shaver blades. It has been found that meniscal tissue may be particularly efficiently resected with the invention described herein.

It is accordingly an object of this invention to produce a rotating shaver blade capable of use as an end cutter.

It is also an object of this invention to produce a rotating end-cutting shaver blade particularly suited for resecting meniscus tissue.

It is a further object of this invention to produce a shaver blade having an end-facing cutting window to facilitate introduction of tissue endwise into the window.

SUMMARY OF THE INVENTION

These and other objects of this invention are achieved by the preferred embodiment disclosed herein which is a surgical tissue resecting instrument comprising elongated inner and outer cylindrical members adapted for relative movement. The cylindrical wall at the distal end of the outer tubular member is provided with at least two notches, each notch having a proximally situated apex and a distally facing notch opening. Each notch further comprises longitudinally extending sides between its apex and opening, each side having a cutting edge lying on the inner circumferential surface of the outer member. The cylindrical wall at the distal end of the inner tubular member is also provided with at least two notches, each having a proximally situated apex and a distally facing notch opening. Each notch further comprises longitudinally extending sides between its apex and its opening, each side having a cutting edge lying on the outer circumferential surface of the inner member. Relative rotation of the inner and outer members will resect tissue presented at the notch openings.

DESCRIPTION OF THE PREFERRED EMBODIMENT

Figure 1:
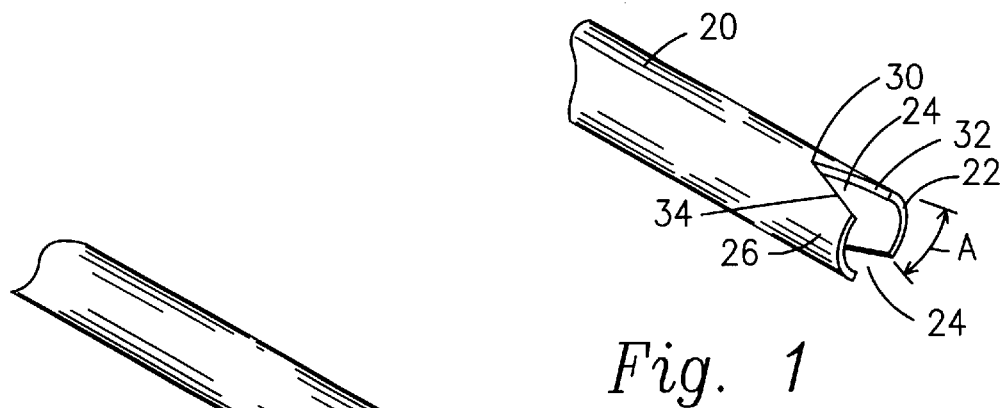
FIG. 1 is a front perspective view of the distal end of an outer tubular member of a shaver blade assembly constructed in accordance with the principles of this invention.
Figure 2:
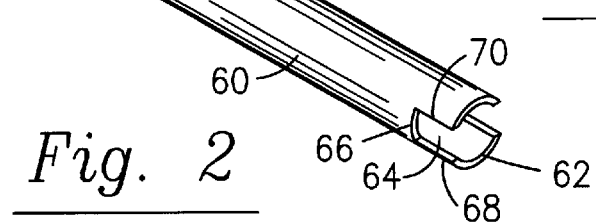
FIG. 2 is a front perspective view of the distal end of an inner tubular member adapted to cooperate with the outer tubular member shown in FIG. 1.
Figure 3:
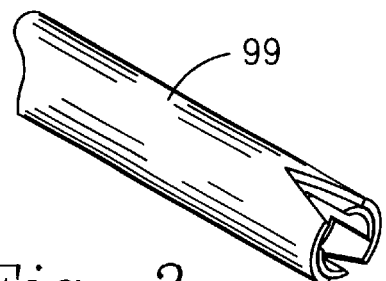
FIG. 3 is a front perspective view of the distal end of a shaver blade assembly formed by combining the tubular assemblies of FIGS. 1 and 2.
Figure 4:
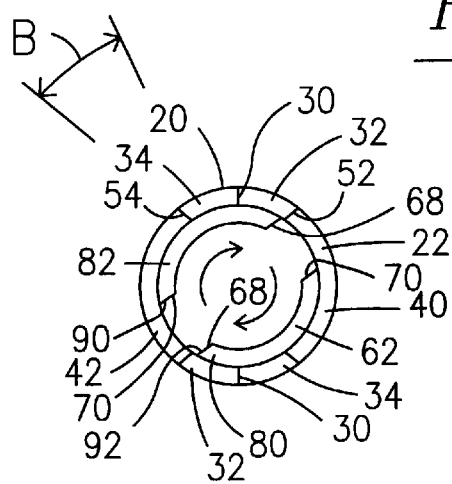
FIG. 4 is an end view of FIG. 3.

Referring to the drawings, FIGS. 1–6 show the structure of the distal end of a shaver blade constructed in accordance with the principles of the invention. The shaver blade outer member 20 terminates in a transverse annular surface 22 and has one or more longitudinally extending cutting windows in the form of V-shaped notches 24 formed in the cylindrical wall 26 of the outer member. It should be noted that the term "longitudinally extending" as used herein means extending generally along the length or axis of the device, whether parallel to the axis or angled relative to the axis. Each notch 24 has a proximal apex 30 and a pair of lateral sides 32 and 34 extending from the apex at a predetermined angle A and terminating at a distally facing notch opening coincident with annular surface 22. It will be understood that annular surface 22 is formed of two arcuate segments 40 and 42 which lie in a plane perpendicular to the axis of outer member 20. As best seen in FIG. 4, lateral side surfaces 32 and 34 are cut at an angle B relative to the axis and the intersections of sides 32 and 34 with arcuate surfaces 40 and 42, respectively, lie along distal-most points 52 and 54, respectively. (In the preferred embodiment points 52 and 54 are actually edges.) In this embodiment apex 30 is a line because of the fact that its side surfaces 32 and 34 have some radial thickness.

As shown in FIG. 2, the distal end of the shaver blade inner member 60 terminates at a transverse annular surface 62. At least one rectilinear notch or cutting window 64 is formed in the distal end of the inner member, each cutting window having a transverse proximal side 66 and a pair of parallel, longitudinally extending side surfaces 68 and 70 terminating at respective distal-most points at a distally facing opening coincident with annular surface 62. It will be understood that annular surface 62 comprises a pair of arcuate segments 80 and 82 each lying in a plane perpendicular to the axis of the inner tubular member. Each side 68 and 70 of the cutting windows 64 is, in the preferred embodiment, shaped so as to lie in a plane parallel to an axial plane of the inner member and intersects arcuate segments 80 and 82 at distal edges 90 and 92.

In the embodiment shown, the shaver blade assembly comprising inner and outer members 60 and 20 comprises a pair of, notches on both inner and outer tubular members. When assembled into a shaver blade assembly 99 as shown in FIG. 3, the annular surface 62 of the inner member coincides longitudinally with the annular surface 22 of the outer member, and as the inner member rotates relative to the outer member, the radially outer edges of the longitudinal sides 68 and 70 of the inner member will resect any tissue presented between them and the radially inner edges of lateral sides 32 and 34 of the notches of the outer member. The edges (which may be called cutting edges) may be sharpened to improve cutting efficiency if necessary. For simplicity, the cutting edges on the inner and outer blades will be referred to as inner and outer cutting edges, respectively, regardless of the fact that they are on the opposite sides (i.e. the inner edge is on the radially outermost side of the inner member and the outer edge is on the radially innermost side of the outer member). The shaver assembly 99 will resect tissue presented laterally to the distal end of the assembly or on axis. If the shaver assembly 99 is used to resect tissue situated in a plane perpendicular to the axis of the assembly, two types of resection patterns may occur. If the assembly is moved distally along its axis into the tissue, it will create a core of tissue within the lumen of the inner member. If the assembly is moved distally along its axis only sufficiently to be brought into contact endwise with the tissue (to a desired depth), and if it is then moved laterally, the tissue will be resected to a desired depth over a desired area.

Figure 5:
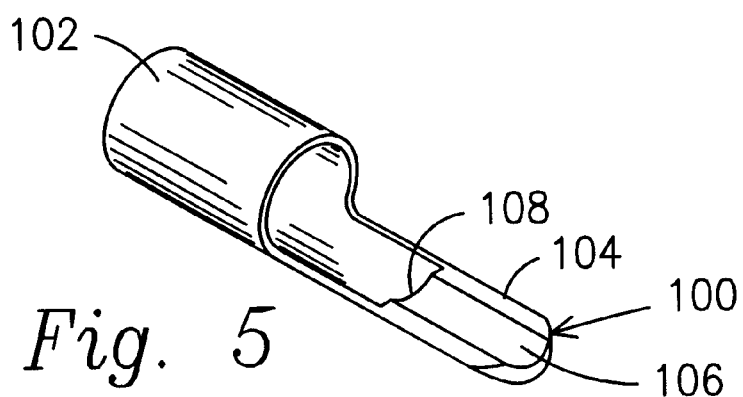
FIG. 5 is a front perspective view of a guide for attachment to the assembly of FIG. 3.
Figure 6:
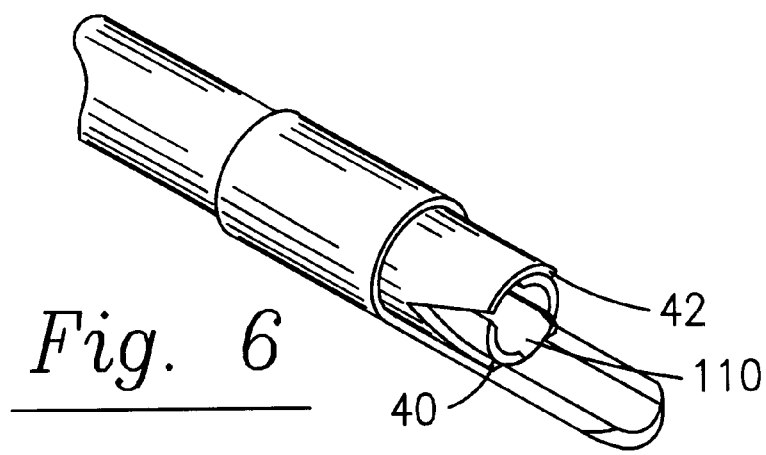
FIG. 6 is a front perspective view of the assembly produced by combining the components of FIGS. 3 and 5.

In another embodiment of the invention as shown in FIGS. 5 and 6, the distal end of the outer tubular member is provided with a guide 100 having a tubular proximal end 102 for being secured to the outer member and a longitudinal arcuate extension 104 which extends longitudinally beyond the distal annular surfaces 22 and 62 of the inner and outer members, respectively. Guide 100 has a longitudinally extending arcuate channel 106 in order to facilitate guiding tissue axially towards the cutting window or tip 110 of the shaver blade assembly for resection. Guide 100 is provided with a proximally facing arcuate shoulder 108 for abutting against a portion of the annular surface 22 of the outer member in order to facilitate the unimpeded movement of tissue into the cutting window. Shoulder 108 is aligned adjacent one of the arcuate segments 40 or 42 and has a thickness equal to that of annular surface 22 to enable tissue to slide along channel 106 and into window 110.

Figure 7:
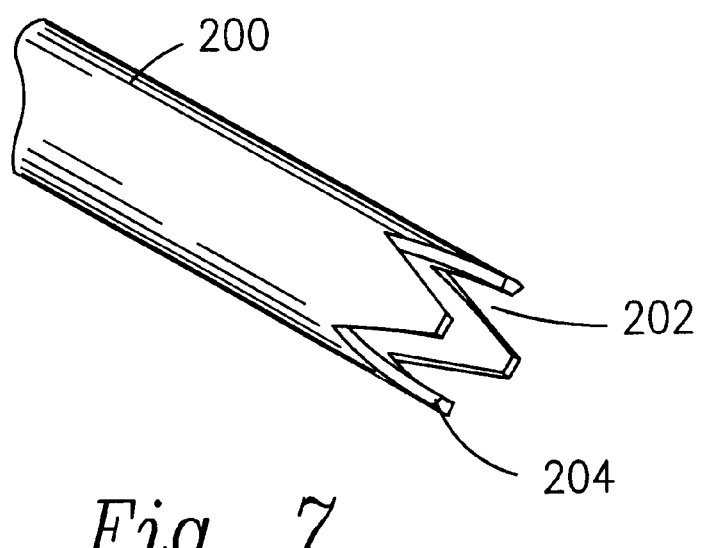
FIG. 7 is a first alternate embodiment of an outer tubular member such as that shown in FIG. 1.
Figure 8:
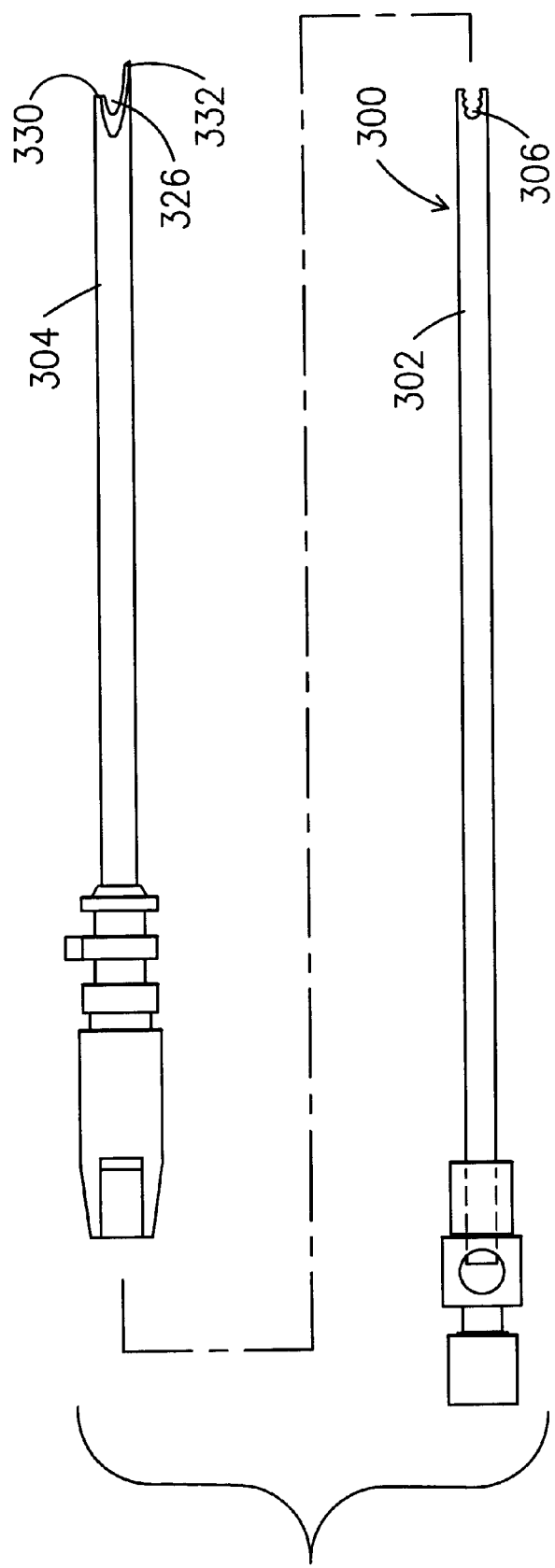
FIG. 8 is an exploded view of a rotatable shaver blade assembly incorporating a second alternate embodiment of the outer tubular member.
Figure 9:
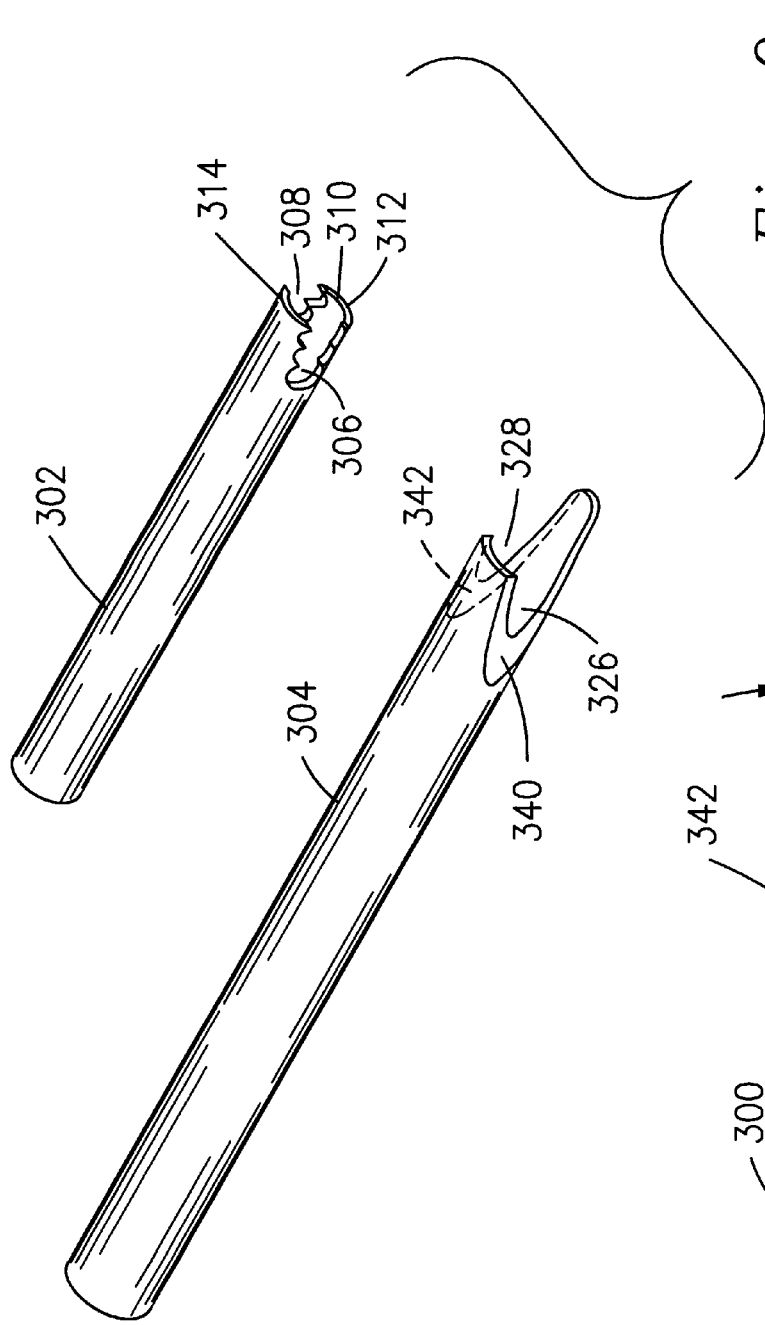
FIG. 9 is a front perspective view of the distal ends of the inner and outer tubular members shown in FIG. 8.

As shown in FIG. 7, the outer tubular member of a shaver blade constructed in accordance with the principles of this invention may be provided with a variety of distal ends. For example, in the first alternate embodiment, outer tubular member 200 is provided with four notches 202 at its distal end. Each notch has an apex and lateral sides as shown in the previous embodiment and terminates at an annular surface 204 at the distal tip of the member 200. It will be understood that annular surface 204 is in the form of a plurality of aligned arcuate segments because of the intersection of the surface with notches 202. The size of the arcuate segments of surface 204 depends upon the number of notches and the angle of the apex of the notches. Indeed, if the apex angle is large enough the arcuate segments 204 will simply be points rather than arcuate surfaces.

It will be understood that the shearing function produced by the passage of the inner and outer notches relative to each other can be produced by also varying the shape of the inner notches. For example, triangular notches could be used on both inner and outer members, and it would be preferable if the included angle of the inner notches were different from that of the outer notches.

A second alternate embodiment of the invention is shown in FIGS. 8 through 11 showing shaver blade assembly 300 comprising an inner tubular member 302 and an outer tubular member 304. Inner tubular member 302 has a pair of diametrically opposed notches 306 and 308 which terminate in a transverse annular surface 310 having arcuate segments 312 and 314. The longitudinally extending sides of notches 306 and 308 are provided with a plurality of teeth 320.

Figure 11:
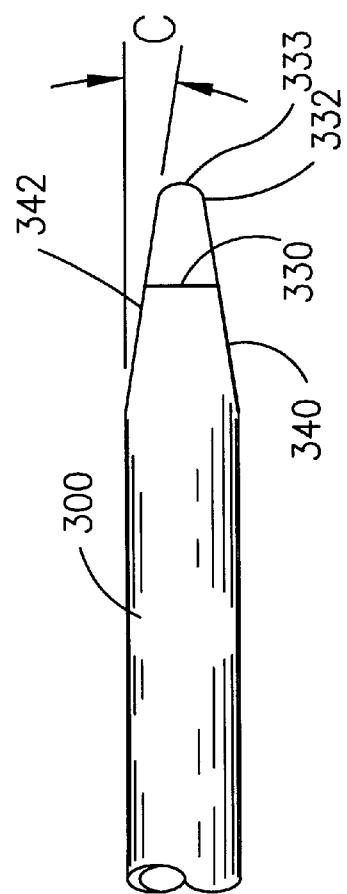
FIG. 11 is a top plan view of FIG. 10.
Figure 10:
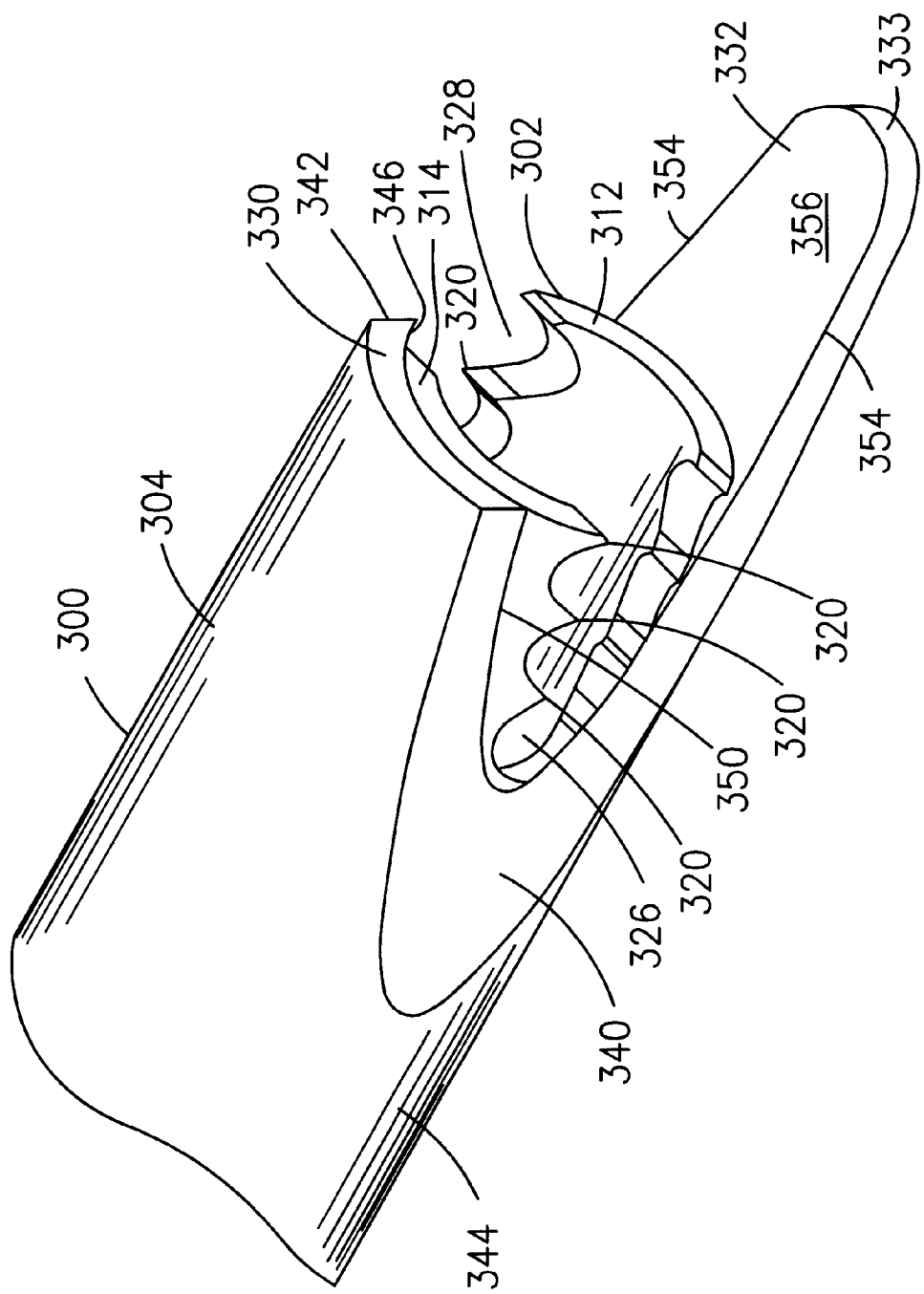
FIG. 10 is a front perspective view of the components of FIG. 8 assembled.

Outer tubular member 304 has a pair of diametrically opposed notches 326 and 328 which terminate at a distally facing arcuate surface 330 along one (top) side of the notches and an integrally formed, elongated guide 332 diametrically opposed from arcuate surface 330 at the other (bottom) side of the notches. As can best be seen from FIGS. 8 and 10, guide 332 has a rounded distal tip 333 and extends a predetermined longitudinal distance beyond arcuate surface 330 in order to guide tissue towards the inner member 302. As best seen in FIGS. 10 and 11, notches 326 and 328 are bounded by symmetrical planar boundary surfaces 340 and 342 extending from the outer tubular member's outer cylindrical surface 344 to its inner cylindrical surface 346. Each surface 340 and 342 is angled at angle C relative to the axis of the tubular member and, in the preferred embodiment, is formed by electrochemically grinding the distal end of the outer tubular member with a grinding wheel having a flat perimetral surface. Other wheel profiles may be used to produce notch boundary surfaces with other than flat surfaces or, as shown in FIGS. 1–7, the boundary surfaces may simply be the outer cylindrical wall of the tube adjacent the notches. The intersection of surfaces 340 and 342 with the inner cylindrical surface creates curved, parabolic-type edges on each side of the outer tubular member. Edges 350 extend between distally facing arcuate surface 330 on one side and guide 332 on the other side. (In effect, guide 332 may be considered an extension added on to an arcuate surface co-planar with and diametrically opposed to arcuate surface 330.) At the guide end, edge 350 runs into edge 354 bounding the top surface 356 of guide 332. It will be noted that, while other edges may be sharpened, edge 354 need not be sharpened because it extends longitudinally beyond the arcuate surfaces 312 and 314 of the inner tubular member so that it does not contribute to tissue resection.

It should also be noted that as the inner member rotates or oscillates relative to the outer member teeth 320 grab tissue to shear it against edge 350. The shape of the notches 326, 328 facilitates tissue resection as the shaver blade assembly is moved distally into tissue. The notch openings are wide enough to accept the tissue and the converging sides of edge 350 urge the tissue toward the apex (proximal-most end) of the notches. The teeth 320 help to keep tissue from being pushed distally as the inner notch edges rotate relative to the outer notch edges. The function of teeth 320 and the notch edges of the inner member is to grab the tissue so it can be urged against cutting edge 350.

In all embodiments each notch at the distal ends of the inner and outer members has a proximally situated apex and longitudinally extending sides extending from the apex to the opening of the notch. In some embodiments, the apex may be a point while in others it may be a more radiused point or even a transverse edge or surface.

It will be understood by those skilled in the art that numerous other modifications and improvements may be made to the preferred embodiments of the invention disclosed herein without departing from the spirit and scope thereof.

What is claimed is:

1. A surgical, tissue resecting instrument comprising:
   an elongated outer cylindrical member having an axis, a cylindrical wall, an open distal end and a proximal end, said cylindrical wall adjacent said distal end of said outer tubular member comprising at least two notches, each having a proximally situated apex and a distally facing notch opening, each said notch further comprising longitudinally extending sides between its apex and opening, each said longitudinally extending side comprising a cutting edge lying on the inner circumferential surface of said outer member, wherein each said notch is bounded on its radially outermost side by a boundary surface, each of said boundary surfaces being planar and symmetrical to each other and situated at a predetermined angle relative to said axis such that said boundary surfaces lie in planes which intersect distally of said open distal end, and wherein said cutting edge of said notch comprises the boundary of said boundary surface with the inner circumferential surface of said outer cylindrical member; and
   an elongated inner cylindrical member adapted to move within said outer tubular member and having a cylindrical wall, an open distal end and proximal end, said cylindrical wall adjacent said distal end of said inner tubular member comprising at least two notches, each having a proximally situated apex and a distally facing notch opening, each said notch further comprising longitudinally extending sides between its apex and its opening, each said longitudinally extending side comprising a cutting edge lying on the outer circumferential surface of said inner member.

2. A surgical, tissue resecting instrument according to claim 1, wherein each apex comprises an arcuate edge and wherein said longitudinally extending sides comprise edges which are arcuate continuations of said arcuate edge.

3. A surgical, tissue resecting instrument comprising:
   an elongated outer cylindrical member having a cylindrical wall, an open distal end and a proximal end, said cylindrical wall adjacent said distal end of said outer tubular member comprising at least two notches, each having a proximally situated apex and a distally facing notch opening, each said notch further comprising longitudinally extending sides between its apex and opening, each said longitudinally extending side comprising a cutting edge lying on the inner circumferential surface of said outer member wherein one of said longitudinally extending sides of each of said notches in said outer tubular member terminates at a first distally facing transverse arcuate surface and wherein the other of said longitudinally extending sides of each of said notches terminates in a second distally facing transverse arcuate surface, said arcuate surfaces being co-planar and diametrically opposed to each other; and
   an elongated inner cylindrical member adapted to move within said outer tubular member and having a cylindrical wall, an open distal end and proximal end, said cylindrical wall adjacent said distal end of said inner tubular member comprising at least two notches, each having a proximally situated apex and a distally facing notch opening, each said notch further comprising longitudinally extending sides between its apex and its opening, each said longitudinally extending side comprising a cutting edge lying on the outer circumferential surface of said inner member; and
   an elongated guide member attached to one of said arcuate surfaces and extending a predetermined longitudinal distance beyond said distally facing arcuate surface.

4. A shaver blade assembly according to claim 3 wherein said guide comprises an integral extension of said cylindrical wall of said outer tubular member.

* * * * *